United States Patent [19]

Perozzi et al.

[11] Patent Number: 4,582,939
[45] Date of Patent: Apr. 15, 1986

[54] MERCAPTAN PRODUCTION

[75] Inventors: Edmund F. Perozzi, Crestwood; Andrew G. Papay, Manchester, both of Mo.

[73] Assignee: Ethyl Petroleum Additives, Inc., St. Louis, Mo.

[21] Appl. No.: 655,756

[22] Filed: Oct. 1, 1984

[51] Int. Cl.$^4$ .......................................... C07C 149/06
[52] U.S. Cl. .................................................... 568/72
[58] Field of Search .......................................... 568/72

[56] References Cited

U.S. PATENT DOCUMENTS

| | | | |
|---|---|---|---|
| 2,386,769 | 10/1945 | Badertscher et al. | 568/72 |
| 2,386,772 | 10/1945 | Badertscher et al. | 568/72 |
| 3,037,052 | 5/1962 | Bortnick | 260/485 |
| 4,347,384 | 8/1982 | Fields | 568/72 |

*Primary Examiner*—Donald G. Daus
*Assistant Examiner*—Mary E. Ceperley
*Attorney, Agent, or Firm*—Donald L Johnson; John F. Sieberth; W. G. Montgomery

[57] ABSTRACT

Catalytic process for the production of mercaptans by contacting unsaturated hydrocarbons with hydrogen sulfide in the presence of a sulfonic acid cation exchange resin catalyst.

7 Claims, No Drawings

MERCAPTAN PRODUCTION

Background of the Invention

This invention relates to a catalytic process for the production of organic sulfur-containing compounds. More particularly, it relates to the production of mercaptans by reacting unsaturated hydrocarbons with hydrogen sulfide in the presence of a specific type of cation exchange resin catalyst. The particular cation exchange resin is a sulfonic acid cation exchange resin which possesses a macro-reticular structure.

It is well known to those skilled in the art that olefins will react with hydrogen sulfide in the presence of an acidic catalyst to form mercaptans. For example, U.S. Pat. No. 2,386,769 discloses a process for producing mercaptans from tertiary base olefins by passing the tertiary base olefin in the vapor phase with hydrogen sulfide through a reaction zone containing a catalyst selected from the acids and thioacids of phosphorous, their anhydrides and thioanhydrides, sulfuric and sulfonic acids and halogenated acids such as trichloroacetic acid. Typically, the catalysts used in these processes are supported catalysts, that is, the active ingredient, for example, a phosphorous compound, is adsorbed on the surface of an inert carrier such as wood charcoal, coconut charcoal, granulated coke, certain clays, and the like as exemplified in the disclosure of aforementioned U.S. Pat. No. 2,386,769. Unsaturated hydrocarbons, however, and particularly tertiary base olefins are notorious for their tendency to polymerize and to compete with the addition reaction to form high boiling poly tertiary base olefins. The polymerized material thus formed builds up on the catalyst support and eventually causes deactivation of the catalyst. After a time, the activity of the catalyst is completely destroyed. Since it is difficult, if is not impossible, to reactivate the catalyst because of the build-up of an impervious or semi-impervious coating of polymerized material on the support, the catalyst must ultimately be discarded and a new one substituted in the process. This is costly, especially if manufacturing is being carried out at plant-size scale and/or the process is continuous.

Thus, an important contribution to the art would be the provision of an acid catalyst which could be used in the production of mercaptans from olefinic material and hydrogen sulfide and one which could be easily reactivated or rejuvenated for reuse in the process. Applicant has found that a particular type of cation exchange resin catalyst, specifically a sulfonic acid cation exchange resin catalyst having a macro-reticular structure can be substituted for conventionally used supported type acid catalysts with no loss in product yield and with the added benefit that the catalyst can be reused over and over again in the process. Although build-up of polymerized material still occurs to some extent on the surface of the cation exchange resins used in the present invention, it is easily and inexpensively removed by treating the catalyst with an aliphatic hydrocarbon such as heptane. Such treatment results in the reactivation of the catalyst so that it is as active or nearly as active as it was when first used.

Other benefits associated with the use of the nuclear sulfonic polymers of the present invention include the convenience with which the catalyst can be separated from the product of the reaction, the lack of corrosion of metal equipment in which the product is made, the need for little or no further purification of the product since the product of the reaction is not contaminated by the catalyst, the ease of reaction and, of course, the economic benefit gained by being able to reactivate, recycle and reuse the catalyst for further mercaptan production.

SUMMARY OF THE INVENTION

In accordance with the present invention, there is provided a catalytic process for converting a tertiary base olefin to the corresponding tertiary mercaptan by contacting the olefin in the vapor phase with hydrogen sulfide in the presence of a sulfonic acid cation exchange resin which possesses a macroreticular structure.

Thus, in one embodiment of the invention there is provided a process for converting a tertiary base olefin to the corresponding tertiary mercaptan which comprises contacting the olefin with hydrogen sulfide in the vapor phase in the presence of a sulfonic acid cation exchange resin which possesses a macroreticular structure whereby the tertiary base olefin is converted to the corresponding mercaptan.

Olefinic hydrocarbons which may be used in accordance with the invention can be represented by the following formula:

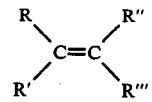

wherein R and R', optionally substituted with functional groups inert to the reaction conditions, are hydrocarbyl groups such as alkyl or alkenyl groups having up to 12 carbon atoms, cycloalkyl or cycloalkenyl groups having from 3 to 12 carbon atoms, optionally branched, or aryl, alkyl-aryl or alkenyl-aryl groups having from 6 to 12 carbon atoms and R" and R'" each represent a hydrogen atom or a hydrocarbyl group as defined above with the proviso that one of either R" or R'" must be hydrogen. The expression "hydrocarbyl group" used herein means a radical derived from a hydrocarbon.

Substituent functional groups, inert to the reaction conditions, are, for instance, halogens (Cl, Br, F, I), and hydroxyl, nitro, alkoxy, amino, carbonyl, carboxylic, esteric, amido and nitrile groups.

As indicated above, R, R' and R" and R'" groups may also be alkenyls; in other words, the process of the invention is applicable also to polyolefins such as dienes and trienes, whether conjugated or not. Specific examples of particularly preferred olefinic reactants include isobutylene, trimethyl ethylene, and unsymetrical methyl ethyl ethylene.

The catalysts which may be used in the invention are sulfonic acid catalysts, such as methane or toluene sulfonic acid and the sulfonated styrene-divinylbenzene copolymers. Such catalysts are commercially available and are used as cation exchange resins. In the present method they are used in their acid form. A particularly preferred cation exchange resin is a nuclear sulfonic acid prepared by sulfonating a copolymer of styrene and a polyvinylidene monomer, such as divinylbenzene, trivinylbenezene, as well as polyvinyl ethers of polyhydric alcohols, such as divinoxyethane and trivinoxypropane. The sulfonating agent typically is concentrated sulfuric acid, oleum, sulfur trioxide or chlorosulfonic acid. For best results, the catalyst should be dehydrated prior to use. One particularly preferred resin catalyst is Amberlyst 15 (registered trademark) which is available from Rohm and Haas Company. For a comprehensive description of the sulfonic acid cation exchange resin catalysts used in the process of the invention and methods by which such catalysts are prepared, see U.S. Pat. No. 3,037,052, all disclosure of which is incorporated herein by reference.

The ratio of moles of resin (defined as the weight in grams of resin per sulfonic acid group) per mole of mixed reactants, i.e., olefin and hydrogen sulfide, can vary widely. In a batch process, the ratios of moles of resin to moles of reactant mixture may vary from 0.001:1 to 0.25:1. A preferred ratio is from 0.02:1 to 0.10:1. In a continuous process, it is difficult to state ratios because one charge of resin can be used for prolonged periods to produce large quantities of mercaptans. In any given section of a packed reactor, however, the ratio of the volume of the resin to the volume of the reactant mixture is substantially 1:1 since the resin typically has approximately 50% void volume.

The proportions of the reactants used in the process can be varied considerably. Theoretically, the optimum molar ratio of olefin to hydrogen sulfide would be 1:1. If desired, however, an excess of hydrogen sulfide can be employed to ensure maximum yield of mercaptan.

High pressures are not required for the invention. Atmospheric, or at the most, pressures only slightly greater than atmospheric are used. In order that the reaction be carried out in the vapor phase, it is necessary that the pressure be less than that pressure at which liquification of the hydrocarbon would occur at the operating temperature. Typically, pressures from atmospheric up to about 5 atmospheres are all that are required to be used in the practice of the invention.

The reaction temperature required for satisfactory conversions will depend on the specific olefins employed. It will also depend to some extent on the reaction time permitted as in the case of batch or continuous processes. The process contemplated herein is operative over a broad temperature range from about room temperature (e.g., 25° C.) up to about 200° C. A preferred range is from about 40° C. to about 130° C. and a most preferred range is from about 60° C. to about 110° C. In many cases, the reaction is exothermic and the desired temperature can be maintained by external cooling.

The reaction time required is a variable value depending for the most part on the specific reactants employed and the temperature and pressure used in the reaction. In general, reaction times of the order of from 0.10 to 15 minutes are suitable when the reaction is carried out in a continuous system, whereas reaction times of the order of from about 15 minutes to 3 or 4 hours may be employed in a batch or static system.

The mercaptans produced by the process of the invention have many applications. For example, some are used as intermediates in the preparation of organic polysulfides which find use as antioxidants for lubricating oils, others have utility as intermediates for the production of organic chemicals, insecticides, germicides and as additives for diesel fuels to improve the cetane number and ignition qualities of the fuel. Organic polysulfides are also useful in the compounding of extreme pressure lubricants and the acceleration of rubber treating processes.

The invention is more fully illustrated by the following examples.

EXAMPLE 1

Tertiary butyl mercaptan was prepared by contacting isobutylene with hydrogen sulfide in the presehce of Amberlyst 15, a polysulfonic acid resin catalyst, the reaction being conducted in a stainless steel tube 5 inches in length having an empty volume of 5.08 cubic centimeters at atmospheric pressure. The reactor was initially charged with 2.12 grams of Amberlyst 15. The reaction was allowed to proceed until the catalyst had lost much of its activity. This took place at the end of approximately 12 hours of continuous running. The rate of flow of the hydrogen sulfide gas was varied between 10.4 and 39.5 milliliters per minute during the operation. The flow rate of the isobutylene gas was varied between 10.4 and 31.9 milliliters per minute during the course of the reaction. The reaction temperature was varied between approximately 73° C. and 108° C. during the course of the run. At the end of each hour, a sample of the exit gas was analyzed by gas chromatography. Most of the tertiary butyl mercaptan was recovered as a liquid by means of external water cooling of a condenser installed at the exit of the catalytic reactor. The remaining uncondensed tertiary butyl mercaptan was detected in the gas phase by gas chromatography. Prior to exhausting the gases to the atmosphere, the gases were scrubbed with caustic to remove unreacted hydrogen sulfide and the small amounts of tertiary butyl mercaptan present in the gas phase. The reaction conditions, yields of tertiary butyl mercaptan and other data measured at the end of each hour of operation is set forth in Table 1 below.

TABLE 1

| Temperature | 93–100° C. | 73–76° C. | 74–76° C. | 94–96° C. | 74–76° C. | 73–75° C. |
| --- | --- | --- | --- | --- | --- | --- |
| Length of Time Elapsed From Start of Reaction | 0.95 hr. | 2 hrs. | 3 hrs. | 4 hrs. | 5 hrs. | 6 hrs. |
| Flow Rate Isobutylene, ml/m | 10.4 | 20.0 | 19.5 | 14.9 | Erratic | 10.7 |
| Flow Rate H$_2$S, ml/m | 10.4 | >17.9 | >19.5 | 20.1 | 26.1 | 17.3 |
| Approx. Conversion | 66% | 86% | 80% | 88% | — | 67% |
| Approx. Yield of Mercaptan | 84% | 52% | 60% | 79% | 82% | 92% |
| Weight of Product | 1.57 gms. | 3.81 gms. | 3.60 gms. | 2.97 gms. | 1.67 gms. | 1.58 gms. |
| Temperature | 76–83° C. | 88–91° C. | 104–108° C. | 89–91° C. | 89–91° C. | 90° C. |
| Length of Time Elapsed From Start of Reaction | 7 hrs. | 8 hrs. | 9 hrs. | 10 hrs. | 11 hrs. | 12 hrs. |
| Flow Rate Isobutylene, ml/m | 24.6 | 31.9 | 28.8 | 29.7 | 26.2 | 27–32 |
| Flow Rate H$_2$S, ml/m | 37.4 | 37.7 | 39.2 | 35.7 | 39.5 | — |
| Approx. Conversion | 59% | 75% | 77% | 70% | 56% | 43% |
| Approx. Yield of Mercaptan | 90% | 86% | 83% | 85% | 82% | 76% |
| Weight of Product | 3.54 gms. | 5.50 gms. | 4.96 gms. | 4.77 gms. | 3.20 gms. | 2.76 gms. |

As shown in the table, the use of a sulfonic and cation exchange resin catalyst produced very good yields of mercaptan (92% highest) and good conversions of reactants to products (88% highest).

EXAMPLE 2

In order to demonstrate the ease with which the resin catalyst can be reactivated, at the end of the 12-hour run described in Example 1, the gas flow to the reactor was shut off and thereafter 50 milliliters of heptane was poured through the reactor over the catalyst at room temperature. The catalyst was then dried at ambient temperature and then at 87° C.–90° C. under nitrogen.

Gas flow of isobutylene and hydrogen sulfide to the reactor was then resumed at 90° C. for a period of 4 hours. The flow rate of the isobutylene varied from 27–32 milliliters per minute and an excess of hydrogen sulfide was present at all times. As in Example 1, measurements and analyses were taken at the end of each hour of the operation. The reaction conditions and results are set forth in Table 2 below.

TABLE 2

| | | | | |
|---|---|---|---|---|
| Temperature | 90° C. | 90° C. | 90° C. | 90° C. |
| Length of Time Elapsed From Heptane Reactivation | 1 hr. | 2 hrs. | 3 hrs. | 4 hrs. |
| Flow Rate Isobutylene, ml/m | 27–32 | 27–32 | 27–32 | 27–32 |
| Approx. Conversion | 62% | 89% | 76% | 79% |
| Approx. Yield of Mercaptan | 86% | 88% | 88% | 87% |
| Weight of Product | 4.29 gms. | 6.09 gms. | 5.72 gms. | 5.89 gms. |

As demonstrated in Table 2, the catalyst activity was rejuvenated by treating the spent catalyst with heptane with yields of mercaptan being restored to 88% (highest) and the conversions of reactants to products being restored to 89% (highest).

We claim:

1. A process for converting a tertiary base olefin to the corresponding tertiary mercaptan which comprises contacting the olefin with hydrogen sulfide in the vapor phase in the presence of a sulfonic acid cation exchange resin which possesses a macro-reticular structure whereby the tertiary base olefin is converted to the corresponding mercaptan and thereafter separating said mercaptan from the reaction product so obtained.

2. The process of claim 1 wherein said olefin is represented by the formula

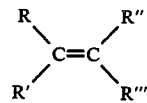

wherein R and R', optionally substituted with functional groups inert to the reaction conditions, are hydrocarbyl groups selected from alkyl or alkenyl groups having up to 12 carbon atoms, cycloalkyl or cycloalkenyl group having from 3 to 12 carbon atoms, branched or unbranched, or aryl, alkyl-aryl or alkenylaryl groups having from 6 to 12 carbon atoms and R" and R''' each represent a hydrogen atom or a hydrocarbyl group as defined above with the proviso that one of either R" or R''' must be hydrogen.

3. The process of claim 2 wherein said olefin is isobutylene, trimethyl ethylene or unsymetrical methyl ethyl ethylene.

4. The process of claim 1 wherein the process is carried out at a temperature ranging from room temperature up to about 200° C.

5. The process of claim 1 wherein an excess of hydrogen sulfide is used in the process.

6. The process of claim 2 wherein said sulfonic acid exchange resin is a dehydrated sulfonic acid exchange resin.

7. A process for the preparation of tertiary butyl mercaptan which comprises contacting isobutylene with hydrogen sulfide in the vapor phase in the presence of a sulfonic acid cation exchange resin which possesses a macro-reticular structure wherein said isobutylene is converted to said tertiary butyl mercaptan and thereafter separating said mercaptan from the reaction product so obtained.

* * * * *